(12) United States Patent
Tang et al.

(10) Patent No.: US 10,545,128 B2
(45) Date of Patent: Jan. 28, 2020

(54) DEVICE FOR MEASURING ADSORPTION/DESORPTION CHARACTERISTIC OF SURFACE BED SEDIMENTS ON CONTAMINANTS AND METHOD OF USING THE DEVICE

(71) Applicant: Hohai University, Jiangsu (CN)

(72) Inventors: Hongwu Tang, Jiangsu (CN); Qingxia Li, Jiangsu (CN); Yang Xiao, Jiangsu (CN); Zhiwei Li, Jiangsu (CN); Saiyu Yuan, Jiangsu (CN)

(73) Assignee: Hohai University, Jiangsu (CN)

( * ) Notice: Subject to any disclaimer, the term of this patent is extended or adjusted under 35 U.S.C. 154(b) by 0 days.

(21) Appl. No.: 16/084,224

(22) PCT Filed: Oct. 10, 2017

(86) PCT No.: PCT/CN2017/105468
§ 371 (c)(1),
(2) Date: Sep. 11, 2018

(87) PCT Pub. No.: WO2018/227828
PCT Pub. Date: Dec. 20, 2018

(65) Prior Publication Data
US 2019/0212318 A1    Jul. 11, 2019

(30) Foreign Application Priority Data

Jun. 12, 2017 (CN) .......................... 2017 1 0438454

(51) Int. Cl.
*G01N 33/24* (2006.01)
*G01N 11/00* (2006.01)
(Continued)

(52) U.S. Cl.
CPC .............. *G01N 33/24* (2013.01); *B01L 3/502* (2013.01); *B01L 3/561* (2013.01); *B01L 5/00* (2013.01);
(Continued)

(58) Field of Classification Search
CPC ....... B01L 2300/047; B01L 2300/0609; B01L 2300/0803; B01L 2300/0832;
(Continued)

(56) References Cited

U.S. PATENT DOCUMENTS

2017/0240446 A1    8/2017   Reid et al.
2018/0364176 A1*  12/2018  Tekleab ................. G01N 31/22

FOREIGN PATENT DOCUMENTS

CN    102372362    3/2012
CN    102590479    7/2012
(Continued)

OTHER PUBLICATIONS

Zhongwei Liu et al., "Effects of riverbed and lake bottom sediment thickness on infiltration and purification of reclaimed water", Environ Earth Sci, Dec. 30, 2016, pp. 1-12.
(Continued)

*Primary Examiner* — Lyle Alexander
*Assistant Examiner* — Bryan Kilpatrick
(74) *Attorney, Agent, or Firm* — JCIPRNET (57) ABSTRACT

The present invention discloses a device for measuring adsorption/desorption of contaminants onto surface bed sediments and a method of using the device. The measurement device includes a sediment sample disc, a sample holder, a reaction cylinder, a liquid collection cylinder, and a liquid circulating member from inside to outside, the liquid circulating member consisting of rubber pipes and a peristaltic pump. According to the method of using the device for measuring the adsorption/desorption of contaminants
(Continued)

onto surface bed sediments, the full contact of bed sediments with pore water and the full exchange of overlying water with pore water are realized through liquid circulation without changing the arrangement modes of the bed sediments; any thickness of bed sediments can be performed on experiments, particularly for thin-layer bed sediments; and natural permeation and accelerated permeation of pore water through bed sediments can be switched simply by adjusting the flow rates of the peristaltic pump and by opening/closing of vent holes. Adsorption characteristic parameters obtained through the device and the method provide, for water quality models, data support which conforms to the natural existing condition of bed sediments and is more scientific and reasonable, and the device and the method achieve significant environmental benefits.

9 Claims, 3 Drawing Sheets

(51) Int. Cl.
*G01N 21/78* (2006.01)
*B01L 3/00* (2006.01)
*B01L 5/00* (2006.01)
*B01L 9/00* (2006.01)

(52) U.S. Cl.
CPC ............... *B01L 9/00* (2013.01); *G01N 11/00* (2013.01); *G01N 21/78* (2013.01); *B01L 2300/047* (2013.01); *B01L 2300/0609* (2013.01); *B01L 2300/0803* (2013.01); *B01L 2300/0832* (2013.01); *B01L 2300/123* (2013.01); *B01L 2400/0481* (2013.01); *B01L 2400/0487* (2013.01)

(58) Field of Classification Search
CPC ....... B01L 2300/123; B01L 2400/0481; B01L 2400/0487; B01L 3/502; B01L 3/561; B01L 5/00; B01L 9/00; G01N 11/00; G01N 21/78; G01N 33/24
See application file for complete search history.

(56) References Cited

FOREIGN PATENT DOCUMENTS

| | | |
|---|---|---|
| CN | 203616304 | 5/2014 |
| CN | 105923962 | 9/2016 |
| CN | 107389896 | 11/2017 |
| KR | 20030062988 | 7/2003 |

OTHER PUBLICATIONS

"International Search Report (Form PCT/ISA/210)", dated Mar. 8, 2018, pp. 1-5.

* cited by examiner

DEVICE FOR MEASURING ADSORPTION/DESORPTION CHARACTERISTIC OF SURFACE BED SEDIMENTS ON CONTAMINANTS AND METHOD OF USING THE DEVICE

CROSS-REFERENCE TO RELATED APPLICATION

This application is a 371 of international application of PCT application serial no. PCT/CN2017/105468, filed on Oct. 10, 2017, which claims the priority benefit of China application no. 201710438454.0, filed on Jun. 12, 2017. The entirety of each of the abovementioned patent applications is hereby incorporated by reference herein and made a part of this specification.

BACKGROUND OF THE INVENTION

Field of the Invention

The present invention belongs to the field of sediment characteristic measurement, and relates to a device for measuring the adsorption/desorption characteristic of sediments on contaminants and a method of using the device.

Description of Related Art

In recent years, the environmental effects of sediments have been increasingly highlighted. The sediments can adsorb/desorb contaminants under different environmental conditions, and become the source and sink of river contaminants, thereby adjusting the water environment. Surface bed sediments are in direct contact with the overlying water body and have a relatively small grain size. They are the main part of bed sediments for adsorption/desorption of contaminants, and have significant environmental effects; therefore, the measurement of the adsorption/desorption characteristic of the surface bed sediments is of great significance in evaluation of a water ecological environment. Most of the river beds, particularly in plain rivers and lakes, consist of cohesive and fine sediments, which have a large adsorption capacity and play an important role in self-adjustment of water ecology. Therefore, it is necessary to provide a reasonable and effective device for measuring the pollutant adsorption/desorption characteristic and a method of using the device according to the features of the surface bed sediments.

Bed sediment mainly adsorb contaminants through interaction with pore water. The contaminants in the overlying water are mainly absorbed/desorbed by bed sediment through ion diffusion and exchange of overlying water with pore water. Therefore, in simulation of adsorption of contaminants in the overlying water body by the surface bed sediments during design of the measurement device, the transport characteristics of contaminants among bed sediments, pore water and overlying water should be taken into full account. Besides, surface bed sediments that play a key role in the migration and transformation of contaminants are generally very thin, and the currently proposed experimental devices for the adsorption/desorption performance of sediments fail to fully consider these features.

The most commonly used method is a batch experiment by using an orbital shaker incubator. Experiments of contaminant adsorption/desorption by a certain quantity of sediments are performed in batches of small containers by using the orbital shaking method, to obtain an isothermal adsorption curve and an adsorption kinetic curve of the sediments. This method is mainly applicable to researches of the adsorption/desorption capability of sediment particles, and cannot derive the adsorption characteristic of the sediments in the arrangement modes of bed sediments and the characteristics of interaction between bed sediments and the pore water. Due to high-frequency oscillation and small reaction space, the sediments fully contact with the contaminants, and the water-sediment contact area is greatly increased, resulting in over-estimation of the contaminant adsorption quantity of the bed sediments, which has a negative effect on the forecast of a water ecological environment. Besides, this method cannot simulate the thickness feature of bed sediments and the permeable boundary thereof, so that the measured adsorption/desorption curve of the sediments differs greatly from the actual situation.

In a conventional soil column experiment, a hole is formed on a side wall of a container accommodating a soil column, and contaminants are injected from one end and are received from the other end, so as to observe migration and transformation of the contaminants in the soil column and the interception capability of soil on the contaminants. This method takes into consideration the permeability of pore water in soil layers, but the container is not a device for quantitatively measuring the adsorption/desorption capability of certain soil layers. The water-sediment contact is inadequate, and the adsorption/desorption quantity of bed sediments in a certain layer cannot be provided quantitatively; therefore, a corresponding isothermal adsorption curve and a corresponding adsorption kinetic curve cannot be drawn. Besides, the permeability of bed sediments simulated by this method is only natural permeation under the effect of gravity, and the permeation pressure on the bed sediments cannot be controlled and adjusted in different working conditions. In normal conditions, the soil column/sediment column is thick and is dozens of centimeters thick, so that it is impossible to perform experimental researches on thin-layer bed sediments.

An invention patent No. "CN 102590479 A" discloses a method and a device for testing the flux of contaminants in river-lake sediments based on a diffusion theory. According to this method, riverbed sediments are placed in a base cylinder, overlying water is injected therein, stratified sampling is performed on the overlying water during different periods of time, and the release flux of contaminants in the sediments is calculated according to a diffusion theory. This method is mainly used for calculating the release flux of bed sediments. The bed sediments are completely static at the bottom of the device, and the overlying water and the pore water can only interact through ion diffusion, without the dynamic exchange between them. Therefore, this method is applicable to a water body with weak hydrodynamic force, for example, a lake where the exchange between the overlying water and the pore water is weak. The bottom boundary of the bed sediments is impermeable, which definitely affects the contact between the lower-layer bed sediments and the pore water, and does not conform to the natural conditions. Just like the conventional soil column experiment, this method cannot quantitatively provide the adsorption/desorption quantity of bed sediments in a certain layer, and therefore, cannot draw a corresponding isothermal adsorption curve and a corresponding adsorption kinetic curve. Meanwhile, this method is applicable to a situation that the thickness of sediments is greater than 5 cm, and is inapplicable to thin-layer bed sediments.

In a circulating water tank experiment, sediments are laid on the bottom of a water tank, and water is enabled to circulate on the surface of the bed sediments under the power provided by a water pump or turbine. This method mainly studies the impact of hydrodynamic flow on adsorption/desorption of sediments and more conforms to the action situation of the hydrodynamic flow in natural conditions. However, this method does not consider the boundary condition that the bottom of the bed sediments is permeable and has a certain permeation pressure, so that the exchange between the pore water and the overlying water is limited, and besides, the experimental device is inapplicable to batch experiments; therefore, an adsorption characteristic curve of the surface bed sediments cannot be drawn.

SUMMARY OF THE INVENTION

The present invention provides a device for measuring the adsorption/desorption characteristic of surface bed sediments on contaminants and a method of using the device, which solves the problems in the prior art that the characteristics of full interaction between surface bed sediments and pore water and full exchange between overlying water and pore water cannot be satisfied, the situation that the bottom boundary of bed sediments is permeable and the permeation pressure is controllable cannot be simulated. Meanwhile, the present invention can perform adsorption/desorption experiments on surface bed sediments of any thickness. The specific technical problems are described as follows:

Although batch experiments can be performed by using a constant-temperature oscillation box to conveniently provide an adsorption/desorption characteristic curve of sediments, the water-sediment contact is over sufficient due to high-frequency oscillation, resulting in a significant increase of the water-sediment contact area and an apparently larger adsorption/desorption quantity of the sediments. Although a conventional sediment column experiment can take into account the permeability of soil layers, it cannot draw a corresponding isothermal adsorption curve and a corresponding adsorption kinetic curve for a certain sediment layer. The permeability of bed sediments simulated by this method is only natural permeation under the effect of gravity, and the permeation pressure cannot be adjusted and controlled. In a method and a device for testing the flux of contaminants in river-lake sediments based on a diffusion theory, dynamic exchange between overlying water and pore water is neglected, a bottom boundary is impermeable, and an isothermal adsorption curve and corresponding characteristic parameters of sediments cannot be obtained. Although a circulating water tank experiment more conforms to the situation of hydrodynamic flow in natural conditions, it rarely considers the boundary condition that the bottom of bed sediments is permeable and has a certain permeation pressure, so that the exchange between pore water and overlying water is limited, and besides, the experimental device is inapplicable to batch experiments; therefore, an adsorption characteristic curve of surface bed sediments cannot be drawn.

To solve the above technical problems, the present invention can be implemented through the following technical solution:

A device for measuring the adsorption/desorption characteristic of surface bed sediments on contaminants is provided, which includes a reaction cylinder, a liquid collection cylinder, and a liquid circulating member from inside to outside. The liquid collection cylinder is a cylinder with a reaction cylinder in the upper part. The upper surface of the reaction cylinder is an opening on the upper surface of the liquid collection cylinder. The reaction cylinder has an opening on the bottom and is suspended in the liquid collection cylinder. Two vent holes are symmetrically provided on the wall of the reaction cylinder and are two thirds of the height of the reaction cylinder away from its bottom. A sample holder and a sediment sample disc are placed inside the reaction cylinder. The liquid circulating member consists of rubber pipes and a peristaltic pump.

The liquid collection cylinder as mentioned-above, the reaction cylinder is formed in the upper part of it. The upper surface of the reaction cylinder is an opening on the upper surface of the liquid collection cylinder, the outer wall of the reaction cylinder is the inner wall of the liquid collection cylinder. The distance from the bottom of the reaction cylinder to the bottom of the liquid collection cylinder is greater than a half of the overall height of the liquid collection cylinder, ensuring that the total volume of the reaction cylinder is smaller than the volume of the lower part of the liquid collection cylinder. During experiments, the total volume of the liquid for reaction should be smaller than the volume of the reaction cylinder; however, in a natural permeation mode, the total volume of the liquid for reaction may exceed the volume of the reaction cylinder, but is smaller than the total volume of the liquid collection cylinder. In this way, after the vent holes are closed, the liquid level in the reaction cylinder is prevented from being too high to cause overflow, and the liquid level in the liquid collection cylinder is also prevented from being too high to cause immersion of the sediment sample disc.

The reaction cylinder as mentioned-above, is in the upper part of the liquid collection cylinder, and the upper surface of it is an opening on the upper surface of the liquid collection cylinder. The diameter of the opening on the bottom surface of the reaction cylinder is smaller than the diameter of the opening on the top surface of the reaction cylinder and the diameter of the bottom surface of the sample holder. In this way, the reaction cylinder can support the sample holder and achieve close connection to the bottom of the sample holder, such that the liquid in the reaction cylinder can completely permeate into the liquid collection cylinder through the bottom of the sediment sample disc.

The sample holder has a frame structure, and the sediment sample disc is placed on the bottom of the sample holder. The bottom of the sample holder is hollow-out and can be woven with a nylon rope, such that the sample holder can support the sediment sample disc, is permeable without changing the permeability of the sediment sample, and makes it convenient to transfer the sediment sample. The diameter of the bottom of the sample holder is slightly smaller than the diameter of the opening on the top of the reaction cylinder, and is greater than the diameter of the opening on the bottom of the reaction cylinder.

In view of the above, the sediment sample disc is placed on the sample holder, and is a hollow cylinder with its diameter being equal to the diameter of the bottom of the sample holder. During experiments, a plastic woven sleeve is fitted on the sediment sample disc from the bottom, and is externally tied with a rubber band. The plastic woven sleeve can ensure the permeability of the bed sediment sample, can simulate the permeation characteristic of the lower boundary of the bed sediments, and meanwhile can fix the bed sediments in the reaction cylinder.

In the liquid circulating member, the two rubber pipes extend from the peristaltic pump, one of the rubber pipes is connected to the bottom of the liquid collection cylinder, and the other is connected to the wall of the reaction cylinder and is closely attached to and fixed on the wall. The liquid in the reaction cylinder on the upper part passes through the sediment sample and enters the lower part of the liquid collection cylinder, while the liquid in the liquid collection cylinder enters the reaction cylinder on the upper part under the power provided by the peristaltic pump, thus forming water circulation in the device. Therefore, full contact of bed sediments and pore water and full exchange of pore water and overlying water are satisfied.

By using the device for measuring the adsorption/desorption characteristic of surface bed sediments on contaminants, the permeation rate (circulation rate of an aqueous solution) of the sediment sample is controllable through control of the opening/closing of the vent holes on the side wall of the reaction cylinder and the flow of the peristaltic pump, such that the permeation pressure of the bed sediments is controllable.

Based on the above, a method of using the device for measuring the adsorption/desorption characteristic of surface bed sediments on contaminants includes the following steps:

1) preparing a bed sediment sample; according to the set thickness of bed sediments, transferring the bed sediment sample of the set thickness to the sediment sample disc fixed with the plastic woven sleeve, or laying the surface layer sediment sample collected on-site in the sediment sample disc fixed with the plastic woven sleeve according to the set thickness; placing the sediment sample disc on the sample holder, and placing the sample holder in the reaction cylinder;

2) setting the flow of the peristaltic pump; if a solution passes through the bed sediment sample in a natural permeation mode, opening the vent holes on the side wall of the reaction cylinder, and calculating the flow of the peristaltic pump by using a natural permeation rate according to a formula below, generally the flow of the peristaltic pump being slightly greater than the permeation flow, where if the liquid level in the reaction cylinder is too high, the solution is discharged into the liquid collection cylinder through the vent holes on the side wall; if the solution passes through the bed sediment sample in an accelerated permeation mode (the set permeation rate is greater than the natural permeation rate), closing the vent holes on the side wall of the reaction cylinder to form a negative pressure in the liquid collection cylinder and accelerate permeation of the pore water, where the flow Q of the peristaltic pump is calculated by using the following formula:

$$Q = \pi/4 \times d^2 \times \upsilon \times 60 \qquad (1),$$

where Q—the flow of the peristaltic pump, mL/min; d—the inner diameter of the sediment sample disc, cm;

$\upsilon$—the permeation rate, cm/s, the natural permeation rate being preliminarily selected as $5 \times 10^{-4}$ cm/s;

3) injecting the prepared liquid of set concentration and volume into the reaction cylinder, turning on the peristaltic pump, and timing the experiment, where the solution in the liquid collection cylinder enters the reaction cylinder through the rubber pipes, and the solution in the reaction cylinder passes through the sediment sample and drips into the liquid collection cylinder, thus forming interaction between the bed sediments and the circulating solution;

4) extracting 10 mL of the liquid from the reaction cylinder by using a needle tube at set times, guiding the extracted liquid through a 0.45 μm aqueous filter membrane; measure the liquid concentration at the set times to obtain an adsorption/desorption kinetic curve of the bed sediments, and use the difference between the initial and final liquid concentration to calculate the adsorption/desorption quantity of sediments; after the experiment ends, air-drying and weighing the bed sediments in the sediment sample disc, to obtain dry weight of the surface bed sediments, such that the adsorption/desorption quantity of the bed sediments per unit mass or per unit area is obtained, and therefore the adsorption/desorption characteristic of the surface bed sediments is obtained.

Particularly, based on the above device, a pore water real-time sampling device can be added in the device. The obtained liquid is mixed pore water that permeates downward within a short term (generally a mean value within 5 to 15 minutes, which depends on the capacity of the pore water sampling member and the downward permeation rate of the pore water), which can obtain the mean concentration of the pore water in the time period. By acquiring the mean concentration of the pore water that permeates downward within a short term, the concentration change of each component in the pore water migrating downward in different working conditions with time can be studied, to obtain the buffering rule of the bed sediments against contaminants.

The real-time measurement of pore water concentration is implemented by arranging a pore water sampling member in the liquid collection cylinder. The pore water sampling part includes a pore water sampling member and a pore water sampling tube. An opening is formed on the side wall of the vessel at the upper part of the pore water collector. One end of the pore water sampling tube is retained in the opening on the side wall of the vessel, and the other end extends out of the device through the vent hole at one side of the reaction cylinder, to facilitate sampling. The diameter of the opening on the side wall of the vessel at the pore water sampling member, the diameter of the vent hole, and the diameter of the pore water sampling tube are consistent, which meets the requirement of air-tightness in the liquid collection cylinder during accelerated permeation and meanwhile facilitates fixing of the pore water sampling tube.

The upper part of the pore water sampling member is a wide and shallow vessel of a small capacity, which stands in the liquid collection cylinder through a middle support rod and a bottom counterweight member. The wide and shallow vessel, the middle support rod, and the bottom counterweight member are fixedly connected. The wide and shallow vessel is used for collecting the liquid directly permeating downward from the sample disc, and the downward permeating liquid overflowed from the vessel flows into the liquid collection cylinder. The support rod is used for holding the vessel at the upper part of the liquid collection cylinder, to avoid mixing with the liquid permeating downward into the liquid collection cylinder before. The counterweight is mainly used for fixing the pore water sampling member to prevent tilting of the pore water sampling member due to buoyancy. During preparation of the experiment, according to the fact whether the pore water needs to be collected in real time, the pore water sampling member is placed in or taken out of the liquid collection cylinder before the experiment starts. The collected liquid reflects the mean concentration of the pore water migrating downward within a period of time which is determined by the capacity of the pore water sampling member. The time t is calculated by using the following formula:

$$t = V/Q \qquad (2),$$

where V—the volume of the wide and shallow vessel at the upper part of the pore water sampling member; Q—the flow of the peristaltic pump after liquid circulation is balanced in the device.

Compared with the prior art, the present invention has the following beneficial effects:

The most significant advantage of the device for measuring the adsorption/desorption characteristic of surface bed sediments on contaminants is that full contact of bed sediments and pore water and full exchange of overlying water and pore water can be realized without changing the existing form of the bed sediments. The device can perform experiments on bed sediments of any thickness, particularly thin-layer bed sediments (below 5 cm thick). Meanwhile, the device can also simulate natural conditions to realize the boundary condition that the bottom of the bed sediments is permeable and has a controllable permeation pressure, and can be switched between natural permeation and accelerated permeation simply by adjusting the flow of the peristaltic pump and by opening/closing of the vent holes. Besides, by adding the pore water sampling member, the mean concentration of the pore water that permeates downward within a short term (generally 5 to 15 minutes) can be obtained in real time, to more comprehensively acquire effect information of the bed sediments on exogenous substances. The peristaltic pump can enable multiple pipelines to work in parallel. The device has a simple structure and is easy to fabricate. It makes possible batch processing of sediments, and thus can more conveniently and rapidly acquire an adsorption kinetic curve, an isothermal adsorption curve, and the adsorption/desorption capacity that conform to natural features of the bed sediments. Adsorption characteristic parameters obtained through the device and the method provide, for water quality models, data support which conforms to the natural existing condition of bed sediments and is more scientific and reasonable, and the device and the method can achieve significant environmental benefits.

BRIEF DESCRIPTION OF THE DRAWINGS

In the drawings, 1—liquid collection cylinder; 2—reaction cylinder; 3—sample holder; 4—sediment sample disc; 5—vent hole; 6—liquid circulating member; 7—rubber pipe; 8—peristaltic pump; 9—pore water sampling member; 10—pore water sampling tube.

DETAILED DESCRIPTION OF THE INVENTION

The present invention is further described in detail below by reference to the specific embodiments and the accompanying drawings.

Figure 1:
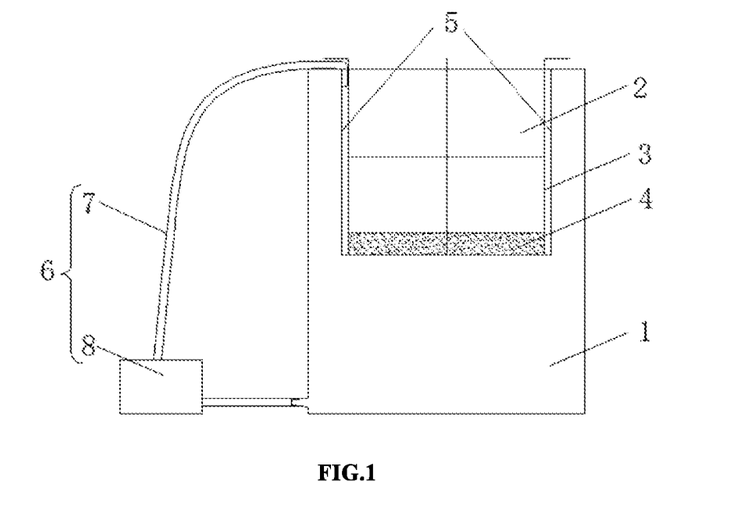
FIG. 1 is a schematic structural diagram of a device for measuring the adsorption/desorption characteristic of surface bed sediments on contaminants according to the present invention.

As shown in FIG. 1, a device for measuring the adsorption/desorption characteristic of surface bed sediments on contaminants includes a sediment sample disc 4, a sample holder 3, a reaction cylinder 2, a liquid collection cylinder 1, and a liquid circulating member 6 from inside to outside. The liquid circulating member 6 consists of rubber pipes 7 and a peristaltic pump 8. The liquid collection cylinder 1 is a cylinder with an opening in the upper part. The reaction cylinder 2 is formed by the opening in the upper part of the liquid collection cylinder 1. The reaction cylinder 2 has an opening on the bottom and is suspended in the liquid collection cylinder 1. Two vent holes 5 are symmetrically provided on the wall of the reaction cylinder 2 and are two thirds of the height of the reaction cylinder away from its bottom. The sample holder 3 is fitted in the reaction cylinder 2 and has a frame structure. The bottom of the sample holder is hollow-out and is connected to the opening on the bottom of the reaction cylinder 2. The sediment sample disc 4 is placed on the sample holder 3, and is a hollow cylinder with its diameter being equal to the diameter of the bottom of the sample holder 3. The two rubber pipes 7 extend from the peristaltic pump 8, one of the rubber pipes is connected to the bottom of the liquid collection cylinder 1, and the other is connected to the wall of the reaction cylinder 2 and is closely attached to and fixed on the wall. The liquid in the reaction cylinder 2 on the upper part passes through the sediment sample and enters the lower part of the liquid collection cylinder 1, while the liquid in the liquid collection cylinder 1 enters the reaction cylinder 2 on the upper part under the power provided by the peristaltic pump 8, thus forming water circulation in the device.

Figure 3:
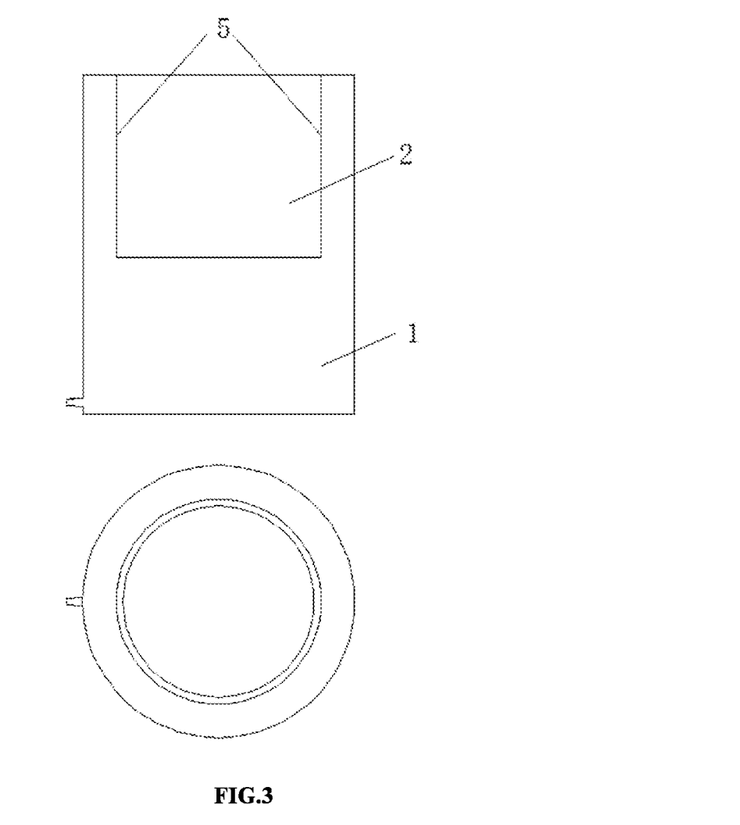
FIG. 3 shows a front view and a top view of a reaction cylinder and a liquid collection cylinder as the main part of the device.

As the reaction cylinder 2 is formed by the opening in the upper part of the liquid collection cylinder 1, the outer wall of the reaction cylinder 2 is the inner wall of the liquid collection cylinder 1, as shown in FIG. 3. The distance from the bottom of the reaction cylinder 2 to the bottom of the liquid collection cylinder 1 is greater than a half of the overall height of the liquid collection cylinder 1, ensuring that the total volume of the reaction cylinder 2 is smaller than the volume of the lower part of the liquid collection cylinder 1. During experiments, the total volume of the liquid for reaction should be smaller than the volume of the reaction cylinder 2. In this way, after the vent holes are closed, the liquid level in the reaction cylinder is prevented from being too high to cause overflow, and the liquid level in the liquid collection cylinder 1 is also prevented from being too high to cause immersion of the sediment sample disc 4.

The diameter of the opening on the bottom surface of the reaction cylinder 2 is smaller than the diameter of the bottom surface of the sample holder 3, and the latter is smaller than the diameter of the opening on the top surface of the reaction cylinder 2, such that the bottom of the reaction cylinder 2 supports the sample holder 3 and is closely connected to the bottom of the sample holder 3. Thereby, the liquid in the reaction cylinder 2 completely permeates into the liquid collection cylinder 1 through the sediment sample in sediment sample disc 4.

Figure 2:
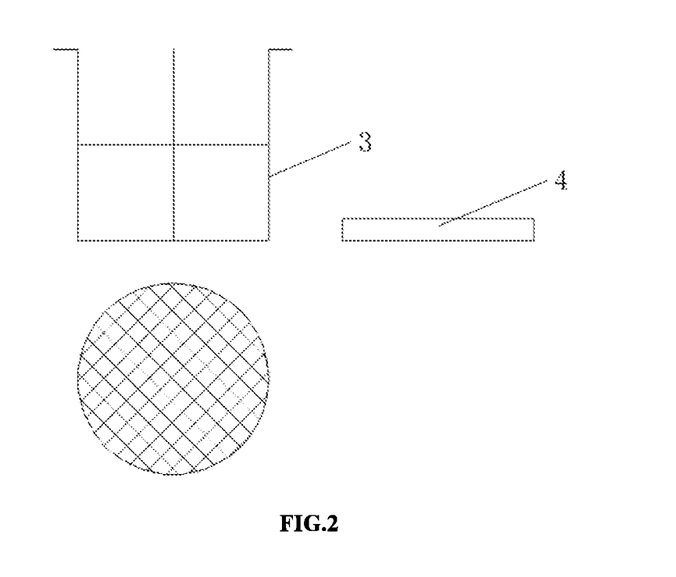
FIG. 2 is a schematic structural diagram of a sample holder and a sediment sample disc.

The frame structure of the sample holder 3 is shown in FIG. 2, and is mainly used for laying and transfer of the bed sediment sample. The bottom of the sample holder is hollow-out and can be woven with a nylon rope to support the sediment sample disc 4. The diameter of the bottom of the sample holder 3 is slightly smaller than the diameter of the opening on the top of the reaction cylinder 2, and is greater than the diameter of the opening on the bottom of the reaction cylinder 2.

The sediment sample disc 4 is placed on the sample holder 3, and is a hollow cylinder, as shown in FIG. 2. The diameter of the sediment sample disc 4 is equal to the diameter of the bottom of the sample holder 3. During experiments, a plastic woven sleeve needs to be fitted on the sediment sample disc from the bottom. The plastic woven sleeve has good permeability and is densely woven to avoid loss of the sediment sample. The woven sleeve is externally tied with a rubber band for fixing. The sediment sample disc 4 is placed on the sample holder 3 and the bed sediment sample is laid thereon. The sediment sample disc 4 is transferred into the reaction cylinder 2 through the sample holder 3.

One of the rubber pipe 7 of the liquid circulating member 6 is sleeved on an outward opening at the bottom of the liquid collection cylinder 1, as shown in FIG. 3. During experiments, the other rubber pipe 7 is closely attached to the side wall of the reaction cylinder 2, and the liquid is injected along the side wall of the reaction cylinder 2, to avoid disturbing the liquid level in the reaction cylinder 2.

In an actual operating process, if the liquid passes through the sediment sample disc 4 in a natural permeation mode, that is, the permeation rate is a natural permeation rate (which may be $5\times10^4$ cmJs for common cohesive soil), the vent holes 5 on the side wall of the reaction cylinder 2 are opened. After the peristaltic pump 8 extracts liquid from the liquid collection cylinder 1, the internal air pressure and the external air pressure of the liquid collection cylinder 1 are equal, and the pore water permeates and drips into the liquid collection cylinder 1 under the effect of gravity. Meanwhile, the flow of the peristaltic pump 8 is set to be slightly greater than the permeation flow calculated by using the formula (1). When the liquid level in the reaction cylinder 2 is too high, the liquid can be discharged into the liquid collection cylinder 1 through the vent holes 5 on the side wall, and the water level in the reaction cylinder 2 is kept above the middle position, ensuring that the water pressure on the bed sediment sample is basically unchanged.

In an actual operating process, if the liquid passes through the sediment sample disc 4 in an accelerated permeation mode, that is, the permeation rate is an accelerated permeation rate, the vent holes 5 on the side wall of the reaction cylinder 2 are closed. After the peristaltic pump 8 extracts liquid from the liquid collection cylinder 1, the pressure in the liquid collection cylinder 1 is reduced to form a negative pressure, and the pore water permeates faster and drips into the liquid collection cylinder 1 under the negative pressure. With an increase in the flow of the peristaltic pump 8, the pressure in the liquid collection cylinder 1 is reduced faster to produce a larger negative pressure, which leads to a greater permeation pressure and a higher permeation rate. The system can operate normally through self-adjustment of the device. The permeation flow of the peristaltic pump can be calculated according to a set permeation rate by using the formula (1). In a specific implementation process, the flow of the peristaltic pump is increased slowly, and the accelerated permeation rate is adjusted according to the permeation capability of the sediment sample.

In a specific example, experimental parameters are generally selected according to features of bed sediments collected on-site, so as to determine the laying thickness of the bed sediment sample, the total volume of the liquid for reaction, and the permeation rate of the liquid. When the liquid permeates in a natural permeation mode, the total volume of the liquid cannot exceed the volume between the vent holes 5 and the bottom of the reaction cylinder 2 (that is, two thirds of the total volume of the reaction cylinder), to ensure normal circulation of the liquid. During the specific design of the size of the reaction cylinder 2, the ratio of the diameter to the depth of the reaction cylinder 2 is set as large as possible, such that the permeation flow can be increased and the time taken for the liquid to circulate once in the device is reduced. If a sample is collected by using a columnar sampler on-site, the diameter of the reaction cylinder 2, the sample holder 3, and the sediment sample disc 4 in the device are determined according to the size of the columnar sampler. The surface layer of the sediment sample in the columnar sampler can be directly transferred into the sediment sample disc 4, to obtain the adsorption/desorption characteristic of the undisturbed sediments on-site.

After the experimental parameters are selected, a method of using the device for measuring the adsorption/desorption characteristic of surface bed sediments on contaminants includes the following steps:

1) preparing a bed sediment sample; according to the set thickness of bed sediments, transferring the bed sediments of the set thickness into the sediment sample disc 4 fixed with the plastic woven sleeve, or laying the surface layer of the bed sediment sample collected on-site in the sediment sample disc 4 fixed with the plastic woven sleeve according to the set thickness of bed sediments for experiment; placing the sediment sample disc 4 on the sample holder 3, and placing the sample holder 3 in the reaction cylinder 2;

2) setting the flow of the peristaltic pump 8; if a liquid passes through the bed sediment sample in a natural permeation mode, opening the vent holes 5 on the side wall of the reaction cylinder 2, and calculating the flow of the peristaltic pump 8 by using a natural permeation rate according to the formula (1), generally the flow of the peristaltic pump 8 being slightly greater than the permeation flow; if the liquid passes through the bed sediment sample in an accelerated permeation mode, closing the vent holes 5 on the side wall of the reaction cylinder 2, and calculating the flow of the peristaltic pump 8 by using a set accelerated permeation rate according to the formula (1), where after the experiment starts, the flow of the peristaltic pump 8 is slowly increased to a preset value;

3) preparing a liquid of the concentration and volume required by the experiment, injecting the liquid completely into the reaction cylinder 2, turning on the peristaltic pump 8, and timing the experiment;

4) extracting 10 mL of the liquid from the reaction cylinder 2 by using a needle tube at set times, guiding the extracted liquid through 0.45 μm aqueous filter membranes; measure the liquid concentration at the set times to obtain an adsorption/desorption kinetic curve of the bed sediments, and use the difference between the initial and final liquid concentration to calculate the adsorption/desorption quantity of sediments. After the experiment ends, air-drying and weighing the bed sediments in the sediment sample disc, to obtain dry weight of the surface bed sediments, such that the adsorption/desorption quantity of the bed sediments per unit mass or per unit area is obtained, and therefore the adsorption/desorption characteristic of the surface bed sediments is obtained.

Particularly, based on the above device, a pore water real-time sampling part can be added in the device. The obtained liquid is a mixed pore water that permeates downward within a short term (generally a mean value within 5 to 15 minutes, which depends on the capacity of the pore water sampling member and the downward permeation rate of the pore water), which can obtain the mean concentration of the pore water concentration in the time period.

Figure 4:
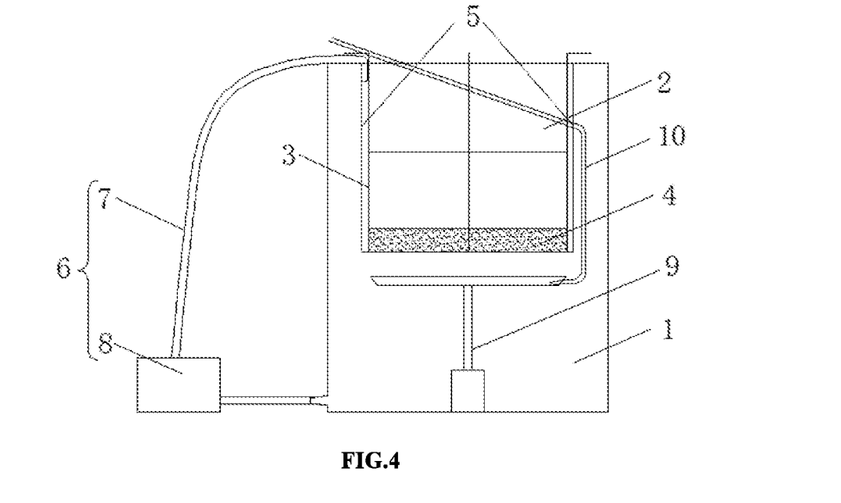
FIG. 4 is a schematic structural diagram of the device after a pore water sampling part is added.
Figure 5:
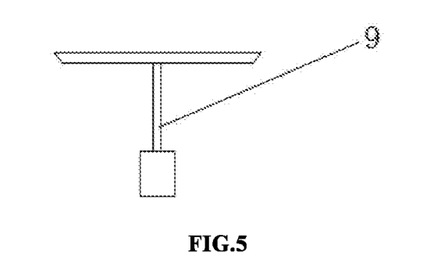
FIG. 5 is a schematic structural diagram of the pore water sampling part.
Figure 6:
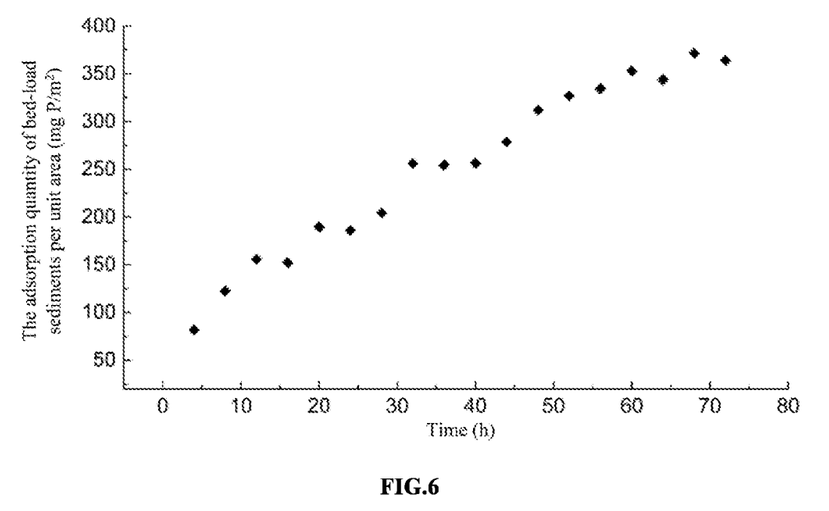
FIG. 6 shows an adsorption kinetic curve of bed sediments per unit area which is obtained by using the measurement device of the present invention according to Example 1.

The pore water real-time sampling part is arranged in the liquid collection cylinder 1 to implement real-time concentration measurement of the pore water migrating downward. The pore water sampling part includes a pore water sampling member 9 and a pore water sampling tube 10. An opening is formed on the side wall of the vessel at the upper part of the pore water sampling member 9. One end of the pore water sampling tube 10 is retained in the opening on the side wall of the vessel, and the other end extends out of the device through the vent hole 5 at one side of the reaction cylinder 2, to facilitate sampling. The diameter of the opening on the side wall of the vessel, the diameter of the vent hole 5, and the diameter of the pore water sampling tube 10 are consistent, which meets the requirement of airtightness in the liquid collection cylinder 1 during accelerated permeation and meanwhile facilitates fixing of the pore water sampling tube 10.

The upper part of the pore water sampling member 9 is a wide and shallow vessel of a small capacity, which stands in the liquid collection cylinder through a middle support rod and a bottom counterweight member. The wide and shallow vessel, the middle support rod, and the bottom counterweight member are fixedly connected. The wide and shallow vessel is used for collecting the liquid directly permeating downward from the sample disc 4, and the downward permeating liquid overflowed from the vessel flows into the liquid collection cylinder 1. The support rod is used for holding the vessel at the upper part of the liquid collection cylinder 1, to avoid mixing with the liquid permeating downward into the liquid collection cylinder 1 before. The counterweight is mainly used for fixing the pore water sampling member 9 to prevent tilting of it due to buoyancy. During preparation of the experiment, according to the fact whether the pore water needs to be collected in real time, the pore water sampling member 9 is placed in or taken out of the liquid collection cylinder 1 before the experiment starts. The collected liquid reflects the mean concentration of the pore water migrating downward within a period of time which is determined by the capacity of the pore water sampling member 9. The time t is calculated by using the following formula:

$$t=V/Q \qquad (2),$$

where V—the volume of the vessel at the upper part of the pore water sampling member; Q—the flow of the peristaltic pump after liquid circulation is balanced in the device.

During the actual operation, the pore water sampling part should be added before the injection of liquid into the liquid collection cylinder 1 and the placement of sediment sample holder 3 in the reaction cylinder 2. The injected liquid should be prevented from entering the vessel at the upper part of the pore water sampling member 9, to avoid affecting the mean concentration of the pore water migrating downward at the initial stage of the experiment.

The batch-type constant-temperature oscillation experiment is a method generally adopted to determine the adsorption characteristic of sediments at present. However, due to small water-sediment reaction space, the water-sediment contact is over sufficient and an apparently larger result is obtained, which has been reported in many articles. According to the method applied in the device provided by CN 102590479 A, bed sediments can only adsorb contaminants through ion diffusion, and the thickness of the sediments cannot be less than 5 cm, such that the adsorption effect of the lower-layer bed sediments is greatly limited and an apparently smaller measurement result is obtained. The balanced adsorption value of sediments obtained through the device of the present invention is basically between the measurement values obtained by using the above two methods in the prior art, particularly for fine sediments.

Besides, the peristaltic pump can enable multiple pipelines to work in parallel. The device has a simple structure and is easy to fabricate. It can implement batch processing of sediments, and thus can more conveniently and rapidly acquire an isothermal adsorption curve and the adsorption/desorption capacity that conform to natural features of the bed sediments.

Example 1

A bed sediment sample is a sediment column collected on-site from the Huai River, and mucky bed sediments on the surface layer are taken for measurement of an adsorption kinetic curve and balanced adsorption quantity. Since the general diameter of a columnar sampler is 9 cm or 12 cm, the diameter of the sediment sample disc can be determined accordingly. The ratio of the diameter and the depth of the reaction cylinder should be as large as possible. In this example, the diameter of the reaction cylinder is 13 cm and the height thereof is 9 cm, two thirds of the volume of the reaction cylinder is 0.8 L, and the diameter of the vent holes on the wall of the reaction cylinder is 1.5 cm; the diameter of the liquid collection cylinder is 17 cm, and the distance from the bottom of the liquid collection cylinder to the bottom of the reaction cylinder is 10 cm; the diameter of the sediment sample disc is 12 cm (which is equal to the diameter of the columnar sampler). The median particle diameter of the sediment sample is 60 µm, the thickness of the sediment sample in the experiment is 2 cm, and the to-be-adsorbed solute is orthophosphate with the concentration of 2 mg/L and the volume of 2 L. The part of the liquid exceeding two thirds of the volume of the reaction cylinder is injected into the liquid collection cylinder through the vent holes. The bed sediment sample is permeated in a natural permeation mode. The specific implementation includes the following steps:

1) A bed sediment sample is prepared, a sediment column collected on-site within 2 cm of the surface layer is directly transferred into the sediment sample disc fixed with the plastic woven sleeve, the sediment sample disc is placed on the sample holder, and the sample holder is placed in the reaction cylinder.

2) The flow of the peristaltic pump is calculated as 3.39 mL/min according to the formula (1), and a value of 3.5 mL/min which is slightly greater than the calculation result of the formula is taken. Since the liquid passes through the bed sediment sample in a natural permeation mode, the vent holes on the side wall of the reaction cylinder are opened.

3) 2 L of a phosphate solution with the concentration of 2 mg/L is injected into the reaction cylinder slowly, the peristaltic pump is turned on, and the experiment is timed. The solution in the liquid collection cylinder enters the reaction cylinder through the rubber pipes, and the solution in the reaction cylinder passes through the sediment sample and drips into the liquid collection cylinder, thus forming interaction between the bed sediments and the circulating solution.

4) 10 mL of the liquid is extracted from the reaction cylinder by using a needle tube at an interval of 4 h, the extracted liquid is guided through a 0.45 μm aqueous filter membrane, the phosphorus concentration in the supernate is measured by using Mo—Sb—Vc colorimetry till the measured concentration stays unchanged. The experiment ends after 72 h, and the bed sediments in the sediment sample disc are air-dried and weighed to obtain the dry weight, which is 215.4 g, of the bed sediments. The difference between the concentration of the phosphorus liquid at a time point in the reaction cylinder and that at the initial time point reflects the adsorption quantity of sediments until this time point, and an adsorption kinetic curve illustrating the change of the phosphorus adsorption quantity of bed sediments per unit area with time can be drawn accordingly. The difference between the initial and final concentration of the phosphorus liquid reflects the adsorption quantity of bed sediments, and the adsorption quantity of bed sediments per unit area under the concentration can be obtained accordingly. The adsorption kinetic curve of bed sediments per unit area is shown in FIG. 4. The balanced adsorption quantity is 358 mg P/m$^2$, which is 18.7 mg P/kg if converted into the adsorption quantity of sediments per unit mass.

In the same working condition, the balanced adsorption quantity of sediments measured by using the batch-type constant-temperature oscillation experimental method and that measured by using the method applied in the device provided by CN 102590479 A are compared with the measurement result obtained by using the device of the present invention. According to the constant-temperature oscillation experiment (the concentration of sediments is 10 g/L and the concentration of the phosphorus solution is 2 mg/L), the obtained adsorption quantity of the bed sediments per unit mass is 81.3 mg P/kg, which is much greater than the measurement result obtained by using the device of the present invention. According to the method applied in the device provided by CN 102590479 A (the thickness of the bed sediments is 5 cm, the diameter thereof is 12 cm, and the dry weight thereof is 532 g; and the volume of the phosphorus solution is 5 L), the obtained phosphorus adsorption quantity of the bed sediments per unit mass is 10.6 mg P/kg, which is apparently smaller than the measurement result obtained by using the device of the present invention. The measurement result obtained by using the device of the present invention is between the measurement results obtained by using the above two devices in the prior art, thus avoiding the problem that the adsorption/desorption quantity of the bed sediments is too large or too small.

To draw an isothermal adsorption curve, the diameter of the sediment sample disc needs to be designed small to facilitate uniform laying of sediments. The peristaltic pump may be a multichannel peristaltic pump. Adsorption experiments are performed under different liquid concentrations to obtain the balanced adsorption quantity, an isothermal adsorption curve is drawn accordingly, and an isothermal adsorption model is used to calculate adsorption characteristic parameters.

As for the desorption experiment of bed sediments, the liquid concentration may be set to zero or an extremely low value, and the change of the liquid concentration is measured at different time to calculate the desorption quantity of the bed sediments.

Example 2

A bed sediment sample is a sediment column collected on-site from the Huai River, and mucky bed sediments on the shallow surface layer are taken for a phosphorus desorption experiment in an accelerated permeation mode. In this example, the diameter of the reaction cylinder s 9.5 cm and the height thereof is 10 cm, the center of each vent hole on the wall is 3 cm away from the top of the reaction cylinder, and the diameter of the vent holes is 0.5 cm. The diameter of the liquid collection cylinder is 12 cm, and the distance from the bottom of the liquid collection cylinder to the bottom of the reaction cylinder is 10 cm. The inner diameter of the sediment sample disc is 9 cm (which is equal to the diameter of a columnar sampler). The pore water sampling member includes a wide and shallow disc, a long support rod, and a solid columnar counterweight. The diameter of the pore water sampling disc is 8 cm and the height thereof is 1 cm, and the volume of the sampling disc is 50 ml. The diameter of a sampling hole on the side wall is 0.5 cm, and the outer diameter of the pore water sampling tube is 0.5 cm, such that the pore water sampling tube can extend out through the vent hole at one side of the reaction cylinder without affecting the air-tightness of the container. The median particle diameter of the sediment sample is 15.6 μm, and the thickness of the sediment sample in the experiment is 8 mm, which is selected for experiment because of the highest content of phosphorus in the shallow surface layer of the bed sediments. The liquid in the experiment is deionized water. Considering the volume taken up by the pore water sampling member and meanwhile ensuring that the opening on the side wall of the liquid collection cylinder is immersed in water, the volume of the liquid is set to 0.8 L to enable water circulation. The bed sediment sample is permeated in an accelerated permeation mode, and the accelerated permeation flow is set to 5 mL/min. The vent hole at one side of the reaction cylinder is sealed by a rubber plug, and the vent hole at the other side allows the pore water sampling tube to pass through. The specific implementation includes the following steps:

1) The device is prepared, the pore water sampling member is placed in the liquid collection cylinder, one end of the pore water sampling tube is retained in the opening on the side wall of the sampling disc, and the other end extends out of the device through the vent hole at one side of the reaction cylinder, to facilitate sampling; the peristaltic pump is connected into the device through the rubber pipes; and 0.4 L of water is directly poured into the liquid collection cylinder (avoiding the pore water sampling disc).

2) A bed sediment sample is prepared. A layer of 8 mm sediment sample at the surface of a sediment column collected on-site is obtained by using a sampling ring, and it is directly transferred into the sediment sample disc fixed with the plastic woven sleeve (since the soil layer is thin, a 0.8 μm filter membrane can be placed above the plastic woven sleeve to prevent loss of fine particles with pore water). The sediment sample disc is placed on the sample holder, and the sample holder is placed in the reaction cylinder.

3) The natural permeation flow of the bed sediment sample is calculated to be approximately 2 mL/min by using a permeation flow formula. As the liquid passes through the bed sediment sample in an accelerated permeation mode and the permeation flow is set to 5 mL/min, the flow of the peristaltic pump is set to 5 mL/min, and the vent hole on the other side of the reaction cylinder is closed.

4) The remaining 0.4 L of deionized water is injected into the reaction cylinder slowly, the peristaltic pump is turned on, and the experiment is timed. The solution in the liquid collection cylinder enters the reaction cylinder through the rubber pipes, and the solution in the reaction cylinder passes through the sediment sample and drips into the liquid collection cylinder, thus forming interaction between the bed sediments and the circulating solution.

5) A needle tube is inserted into the pore water sampling tube to extract 25 mL of a pore water sample at 0.25 h, 24 h, 48 h, 72 h, 96 h and 120 h (the volume of the sample is high due to its low concentration), and the sample reflects the mean concentration of the pore water within 10 min before sampling. Besides, 10 ml of liquid in reaction cylinder (overlying water) is also extracted at those time point. The extracted solution is guided through a 0.45 μm aqueous filter membrane, and the phosphorus concentration in the supernate is measured by using Mo—Sb—Vc colorimetry. The buffering effect of the bed sediments on the phosphorus is obtained through comparison of the concentration of the overlying water and pore water.

Figure 7:
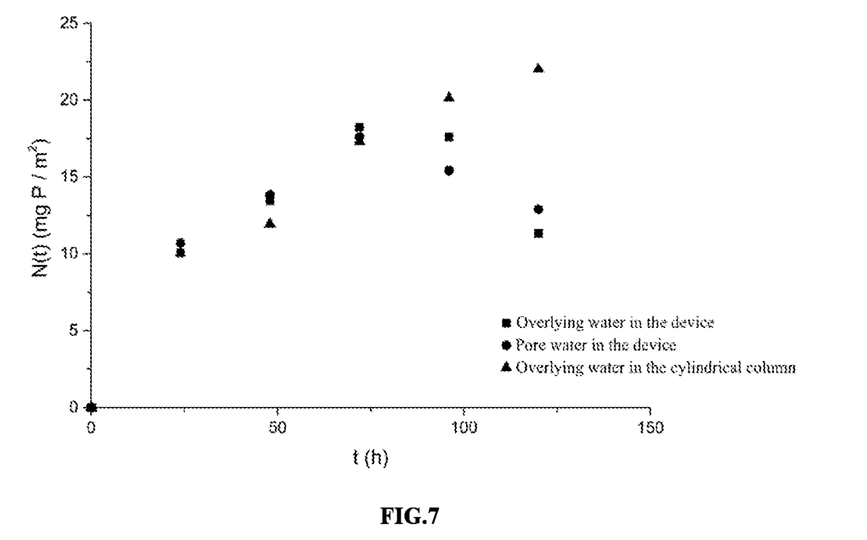
FIG. 7 shows a curve illustrating the change of the release quantity of bed sediments per unit area with time which is obtained by using the measurement device of the present invention according to Example 2, and shows comparison with a standing and release process of bed sediments in a cylindrical column.

After the experiment ends, the bed sediments in the sediment sample disc are air-dried and weighed to obtain the dry weight, which is 47.3 g, of the bed sediments. According to the concentration change of the pore water and overlying water at different time points, a phosphorus release curve of the bed sediments interacting with the deionized purified water can be obtained preliminarily. The difference between the initial concentration and the final concentration of the overlying water when the experiment ends reflects the desorption quantity of the bed sediments, and the desorption quantity of bed sediments per unit area under the concentration can be obtained accordingly. The change of the desorption quantity of the bed sediments per unit area with time is shown in FIG. 7. When the experiment ends, the desorption quantity is 11.3 mg P/m$^2$, which is 1.52 mg P/kg if converted into the desorption quantity of sediments per unit mass.

An experiment is performed in a cylindrical column with the inner diameter of 9 cm under the same working condition, in which the thickness of the surface bed sediments is 8 mm and the volume of the deionized water is 0.8 L. The experimental result is compared with the measurement result obtained by using the device of the present invention. The comparison result is shown in FIG. 7. The bed sediments in the cylindrical column remain in a release state, and the obtained desorption quantity of the bed sediments per unit mass is 2.96 mg P/kg, which is nearly twice as much as the measurement result obtained by using the device of the present invention. The adsorption characteristic of the bed sediments obtained through the device of the present invention is that the bed sediments release first and adsorb again when the liquid concentration is high, thus forming a dynamic adsorption/desorption process. Therefore, more adsorption/desorption characteristics of sediments can be obtained through the device of the present invention, and the buffering mechanism of bed sediments in natural rivers on various types of contaminants can be obtained accordingly.

The parts not described in the present invention are the same as those in the prior art or are implemented by using the prior art.

The foregoing embodiments merely describe the technical idea of the present invention, but are not intended to limit the protection scope of the present invention. Any modification made based on the technical solutions and according to the technical idea provided by the present invention falls within the protection scope of the present invention.

What is claimed is:

1. A device for measuring the adsorption/desorption characteristic of surface bed sediments on contaminants, comprising a sediment sample disc, a sample holder, a reaction cylinder, a liquid collection cylinder, and a liquid circulating member from inside to outside, the liquid circulating member consisting of rubber pipes and a peristaltic pump, wherein the reaction cylinder is a cylindrical cavity formed in an upper part of the liquid collection cylinder, an upper surface of the reaction cylinder is an opening on an upper surface of the liquid collection cylinder and an outer wall of the reaction cylinder is an inner wall of the liquid collection cylinder; the reaction cylinder has an opening on the bottom and is suspended in the liquid collection cylinder, a distance from the bottom of the reaction cylinder to the bottom of the liquid collection cylinder is greater than a half of the overall height of the liquid collection cylinder, and vent holes are provided on a wall of the reaction cylinder; the sample holder is fitted in the reaction cylinder and has a frame structure, the bottom of the sample holder is hollow-out and is connected to the opening on the bottom of the reaction cylinder; the sediment sample disc is placed on the sample holder, and is a hollow cylinder with its diameter being equal to the diameter of the bottom of the sample holder; two rubber pipes extend from the peristaltic pump, one of the two rubber pipes is connected to the bottom of the liquid collection cylinder, and the other one of the two rubber pipes is connected to the wall of the reaction cylinder and is closely attached to and fixed on the wall; liquid in an upper part of the reaction cylinder passes through a sediment sample and enters a lower part of the liquid collection cylinder, while the liquid in the liquid collection cylinder enters the upper part of the reaction cylinder under the power provided by the peristaltic pump, thus forming a water circulation in the device.

2. The device for measuring the adsorption/desorption characteristic of surface bed sediments on contaminants according to claim 1, wherein the diameter of an opening on a bottom surface of the reaction cylinder is smaller than the diameter of a bottom surface of the sample holder and the diameter of the bottom surface of the sample holder is smaller than the diameter of an opening on a top surface of the reaction cylinder, such that the bottom of the reaction cylinder supports the sample holder and is closely connected to the bottom of the sample holder, and thereby, the liquid in the reaction cylinder completely permeates into the liquid collection cylinder through a bottom of the sediment sample disc.

3. The device for measuring the adsorption/desorption characteristic of surface bed sediments on contaminants according to claim 1, wherein two vent holes are symmetrically provided on the wall of the reaction cylinder and are two thirds of the height of the reaction cylinder away from the bottom of the reaction cylinder.

4. The device for measuring the adsorption/desorption characteristic of surface bed sediments on contaminants according to claim 1, wherein a plastic woven sleeve is fitted on the sediment sample disc from a bottom of the sediment sample disc, and is externally tied with a rubber band.

5. The device for measuring the adsorption/desorption characteristic of surface bed sediments on contaminants according to claim 1, wherein a permeation rate of the sediment sample is controllable through control of the opening/closing of the vent holes on the wall of the reaction cylinder and a flow of the peristaltic pump, such that a permeation pressure of the bed sediments is controllable.

6. A method of using the device for measuring the adsorption/desorption characteristic of surface bed sediments on contaminants according to claim 1, comprising the following steps:
preparing a bed sediment sample; according to a set thickness of bed sediments for experiment, transferring the sediment sample to the sediment sample disc fixed with a plastic woven sleeve, or laying a surface layer of bed sediment sample collected on-site in the sediment sample disc fixed with the plastic woven sleeve according to the set thickness of the bed sediments for experiment; placing the sediment sample disc on the sample holder, and placing the sample holder in the reaction cylinder;

setting a flow of the peristaltic pump; wherein if a liquid passes through the bed sediment sample in a natural permeation mode, the vent holes on the wall of the reaction cylinder are opened, and the flow of the peristaltic pump is calculated by using a natural permeation rate according to a formula below, the flow of the peristaltic pump being greater than the permeation flow; if the liquid passes through the bed sediment sample in an accelerated permeation mode, the vent holes on the wall of the reaction cylinder are closed, and the flow of the peristaltic pump is calculated by using a set accelerated permeation rate according to the formula below, wherein after the experiment starts, the flow of the peristaltic pump is increased to a preset value;

the flow of the peristaltic pump is calculated by using the following formula:

$$Q = \pi/4 \times d^2 \times \upsilon \times 60$$

wherein Q is the flow of the peristaltic pump, mL/min; d is the inner diameter of the sediment sample disc, cm;
$\upsilon$ is the permeation rate, cm/s, a natural permeation rate being preliminarily selected as $5 \times 10^{-4}$ cm/s;

injecting a liquid prepared for reaction completely into the reaction cylinder, turning on the peristaltic pump, and timing the experiment;

extracting 10 mL of the liquid from the reaction cylinder by using a needle tube at set times, guiding the extracted liquid through a 0.45 μm aqueous filter membrane; measuring a concentration of the liquid at these times to obtain an adsorption/desorption kinetic curve of the bed sediments, and using the difference between the initial and final concentration of the liquid to calculate an adsorption/desorption quantity of sediments; after the experiment ends, air-drying and weighing the bed sediments in the sediment sample disc, to obtain dry weight of the surface bed sediments, such that the adsorption/desorption quantity of the bed sediments per unit mass or per unit area is obtained, and therefore the adsorption/desorption characteristic of the surface bed sediments is obtained.

7. The device for measuring the adsorption/desorption characteristic of surface bed sediments on contaminants according to claim 1, wherein the device is further provided with a pore water real-time sampling part comprising a pore water sampling member and a pore water sampling tube; an upper part of the pore water sampling member is a wide vessel, which stands in the liquid collection cylinder through a middle support rod and a bottom counterweight member; the wide vessel, the support rod, and the counterweight member are fixedly connected, the wide vessel is configured for collecting the liquid directly permeating downward from the sample disc, the middle support rod is configured for holding the vessel at an upper part of the liquid collection cylinder, and the bottom counterweight is configured for fixing the pore water sampling member; an opening is formed on a side wall of the vessel at the upper part of the pore water sampling member, one end of the pore water sampling tube is retained in the opening on the side wall of the vessel at the upper part of the pore water sampling member, and the other end extends out of the device through the vent hole at one side of the reaction cylinder; the diameter of the opening on the side wall of the vessel, the diameter of the vent hole, and the diameter of the pore water sampling tube are consistent.

8. The method of using the device for measuring the adsorption/desorption characteristic of surface bed sediments on contaminants according to claim 6, further comprising a step of preparing the device before preparing the bed sediment sample, wherein a pore water sampling member is placed in the liquid collection cylinder, one end of the pore water sampling tube is retained in the opening on the side wall of the vessel at an upper part of the pore water sampling member, and the other end extends out of the device through the vent hole at one side of the reaction cylinder; the peristaltic pump is connected into the device through the rubber pipes; and water is directly poured into the liquid collection cylinder while avoiding a wide vessel at the upper part of the pore water sampling member.

9. The device for measuring the adsorption/desorption characteristic of surface bed sediments on contaminants according to claim 3, wherein a permeation rate of the sediment sample is controllable through control of the opening/closing of the vent holes on the wall of the reaction cylinder and a flow of the peristaltic pump, such that a permeation pressure of the bed sediments is controllable.

* * * * *